United States Patent [19]

Segrest et al.

[11] Patent Number: 4,643,988

[45] Date of Patent: Feb. 17, 1987

[54] AMPHIPATHIC PEPTIDES

[75] Inventors: Jere P. Segrest; Gattadahalli M. Anantharamaiah, both of Birmingham, Ala.

[73] Assignee: Research Corporation, New York, N.Y.

[21] Appl. No.: 610,444

[22] Filed: May 15, 1984

[51] Int. Cl.[4] .................. A61K 37/43; C07K 7/08; C07K 7/10
[52] U.S. Cl. ........................ 514/12; 514/13; 530/324; 530/326
[58] Field of Search ............ 260/112.5 R; 514/12, 514/13; 530/324, 326

[56] References Cited

PUBLICATIONS

Kaiser et al., PNAS, USA 80: 1137–1143 (1983); Science 223: 249–51 (1984).
Sparrow et al., Peptides Eds, Rich & Gross, pp. 253–256 (1981).
Kanellis et al., Jour. Biol. Chem. 255, 11464–11472 (1980).
Segrest et al., Jour. Biol. Chem. 258: 2290–2295 (1983).

Primary Examiner—Delbert R. Phillips
Attorney, Agent, or Firm—Scully, Scott, Murphy & Presser

[57] ABSTRACT

The present invention relates to peptides of the formula

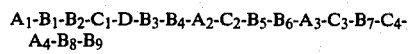

$A_1$-$B_1$-$B_2$-$C_1$-D-$B_3$-$B_4$-$A_2$-$C_2$-$B_5$-$B_6$-$A_3$-$C_3$-$B_7$-$C_4$-$A_4$-$B_8$-$B_9$ wherein:
$A_1$, $A_2$, $A_3$ and $A_4$ are independently aspartic acid or glutamic acid, or homologues or analogues thereof; $B_1$, $B_2$, $B_3$, $B_4$, $B_5$, $B_6$, $B_7$, $B_8$ and $B_9$ are independently tryptophan, phenylalanine, leucine, alanine, tyrosine, isoleucine, valine or α-naphtylalanine, or homologues or analogues thereof; $C_1$, $C_2$, $C_3$, and $C_4$ are independently lysine or arginine, or homologues or analogues thereof, and D is serine, threonine, alanine, glycine, or histidine; provided that, when $A_1$ and $A_2$ are aspartic acid, $A_3$ and $A_4$ are glutamic acid, $B_2$ and $B_7$ are leucine, $B_3$ and $B_9$ are phenylalanine, $B_4$ is tyrosine, $B_5$ is valine, and $C_1$, $C_2$, $C_3$ and $C_4$ are lysine, and $B_6$, $B_8$ and D are alanine, $B_1$ is not tryptophan. These peptides are useful in the treatment and prevention of atherosclerosis.

7 Claims, 9 Drawing Figures

Comparison of Natural and Synthetic Amphipathic Domains

LCAT reaction on the discoidal recombinant apo A-I/egg PC-cholesterol an I/egg PC-cholesterol.

Density Gradient Ultracentrifugation

Distribution of protein and phospholipid in the density gradient fractions of I/QMPC complexes, I, DMPC and apo A-DMPC complexes.

PEPTIDE-DMPC COMPLEXES
ELECTRON MICROGRAPH

APO A-I-DMPC COMPLEXES
ELECTRON MICROGRAPH

AMPHIPATHIC PEPTIDES

FIELD OF THE INVENTION

The present invention relates to novel peptides; in particular, it relates to novel peptides useful in the treatment and prevention of atherosclerosis. The invention described herein was made in the course of a work under a grant or award from the Department of Health and Human Services. The U.S. Government is entitled to a nonexclusive, royalty-free license.

BACKGROUND OF THE INVENTION

Among the most common and critical health problems in the United States today is atherosclerosis, and its attendant complications, in particular, coronary heart disease. A number of risk factors have been implicated in the development of "premature" atherosclerosis, one of the most important of these being elevated plasma cholesterol. Because of the crucial role that cholesterol appears to play in the occurrence of heart disease, a great deal of attention has been devoted to the study of its metabolism in the human body.

Of particular recent interest is the investigation of the relationship between the levels of plasma lipoproteins or serum lipids and the risk of development of coronary heart disease. Both high density lipoproteins (HDL) and low density lipoproteins (LDL) are carriers of cholesterol in the form of cholestryl esters. There is some indication, however, that while LDL cholesterol is a positive risk factor (Kannel et al., Ann Intern Med 90:85-91, 1979), HDL is an even more important negative risk factor (see FIG. 1). Although the exact functions of these lipoproteins are not completely determined, it appears that HDL serves particularly to remove cholesterol from peripheral cells, and transport it back to the liver, where a large proportion of the cholesterol excreted from the body is removed.

One current idea on the specific roles of LDL and HDL in the development of cardiovascular disease emphasizes the role of the overloading of the lysosomes of the cells of the arterial walls with metabolites which are generally hydrolyzed rather slowly, specifically cholesteryl esters and triglycerides. These are transported from the liver and intestine by plasma LDL. Should the amount of these lipids exceed the capacity of the HDL for transporting them to the liver for excretion, cells in certain critical areas, such as the arterial wall, become gorged with cholestryl esters. This overloading eventually results in impaired cell function, and, if continued, cell death. The continued overloading further results in the accumulation of cellular debris, and the formation of atherosclerotic plaque in the vessel wall. This in turn may lead to blockage of the artery, and spasms of the muscular layer, events which may manifest themselves as coronary heart disease or strokes.

Each of the known plasma lipoproteins is formed by the association of one or more apoprotein moieties with phospholipid. Considerable attention has been given in recent years both to the role of the apoproteins in the overall function of the lipoprotein, and to its manner of association with the lipid. There is much evidence to suggest that the protective effect of HDL may be due to participation in the process of reverse cholesterol transport, which is in turn dependent upon the levels of the major HDL apoprotein component, A-I. The latter has the effect of stimulating lecithin:cholesterol acyl transferase activity, which is important in concentrating cholestrol, in the form of cholesteryl ester, inside the HDL particles.

A mechanism to explain certain features of protein lipid interactions in the plasma lipoproteins has been suggested in the amphipathic helix hypothesis (Segrest et al., FEBS Letter, 38:247-253, 1974). This model suggests a general structural arrangement of amino acid residues which result in helical domains, called amphipathic helices, containing polar and non-polar faces. A general distribution of the charged residues was proposed, with the positive occurring along the interface between the polar and non-polar faces, and the negative along the center of the polar face. This arrangement of the charged residues allows the lysine or arginine acyl side chains to contribute to the hydrophobicity of the non-polar face. The charged residues also seem to form topographically close complementary ion pairs, the number of which may be significant. Further, this model allows for ionic interactions between positively charged side chains and the phosphate group of the phospholipid, as well as between negatively charged residues and positively charged groups on the phospholipid. Such interactions may play a role in initiating or contributing to the stability of the peptide-lipid complex.

Given this proposed model, it should theoretically be possible to attempt construction of synthetic analogs of apo A-I which are capable of functioning in much the same way as the model apolipoprotein. In order to act as a satisfactory substitute for APO A-I, a synthetic peptide would be required to (1) form small, stable, discoidal complexes with phospholipid, as apo A-I does normally in nascent HDL, and (2) stimulate lecithin-cholestryl acyl transferase (LCAT) activity. It should also preferably be able to displace native apolipoprotein, particularly APO A-I, from HDL complexes.

Recently, various synthetic functional apolipoprotein analogues have been reported. Sparrow, et al. (Peptides, Eds, Rich & Gross, p. 253-256, 1981) have produced a series of "Lipid Associating Peptides" (LAP) which have been shown to activate LCAT. Although it is assumed from this evidence that these peptides would have a high affinity for lipids, there are no numerical data which conclusively support this assumption. Kaiser and Kezdy (PNAS, USA 80:1137-1143; 1983; Science 223:249-251, 1984) also disclose amphipathic peptides which have been shown, to some extent, to mimic the activity of apo A-I. Kanellis et al. (Jour Biol. Chem. 255:11464-11472, 1980), and Segrest et al. (Jour Biol. Chem. 258:2290-2295, 1983) have described an amphipathic peptide, 18 As, which exhibit LCAT activation and the ability to displace native apolipoprotein from HDL complexes. None of these peptides, however, has been as yet shown to form stable, discoidal, nascent, HDL-like complexes with phospholipids, a feature which is critical to their utility as components of pharmaceutically useful synthetic lipoproteins.

It has now been discovered that a new series of peptides exhibit an unexpected improvement over previously known peptides in their ability to mimic apo A-I activity. These new peptides not only are capable of stimulating LCAT activity and displacing apolipoprotein from native HDL, but also displace a higher percentage of apolipoprotein than known amphipathic peptides, and are the first to demonstrate the capacity for forming compact, discoidal nascent HDL-like complexes. As noted above, the latter characteristic is particularly important to the peptides' contemplated role in the treatment of atherosclerosis by the administration of synthetic HDL complexes.

BRIEF DESCRIPTION OF THE INVENTION

The present invention relates to peptides capable of forming an amphipathic helix which contain the sequence

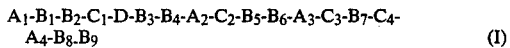

$$A_1\text{-}B_1\text{-}B_2\text{-}C_1\text{-}D\text{-}B_3\text{-}B_4\text{-}A_2\text{-}C_2\text{-}B_5\text{-}B_6\text{-}A_3\text{-}C_3\text{-}B_7\text{-}C_4\text{-}A_4\text{-}B_8\text{-}B_9 \quad (I)$$

wherein:

$A_1$, $A_2$, $A_3$ and $A_4$ are independently aspartic acid or glutamic acid, or homologues or analogues thereof; $B_1$, $B_2$, $B_3$, $B_4$, $B_5$, $B_6$, $B_7$, $B_8$ and $B_9$ are independently tryptophan, phenylalanine, alanine, leucine, tyrosine, isoleucine, valine or $\alpha$-naphthylalanine, or homologues or analogues thereof; $C_1$, $C_2$, $C_3$ and $C_4$ are independently lysine or arginine, and D is serine, threonine, alanine, glycine, histidine, or homologues or analogues thereof;

provided that, when $A_1$ and $A_2$ are aspartic acid, $A_3$ and $A_4$ are glutamic acid, $B_2$ and $B_9$ are leucine, $B_3$ and $B_7$ are phenylalanine, $B_4$ is tyrosine, $B_5$ is valine, $B_6$, $B_8$, and D are alanine, and $C_1$, $C_2$, $C_3$ and $C_4$ are lysine, $B_1$ is not tryptophan.

It further relates to the use of the novel peptides in the formation of substitute high density lipoproteins useful in the treatment of atherosclerosis.

DETAILED DESCRIPTION OF THE INVENTION

Figure 1:
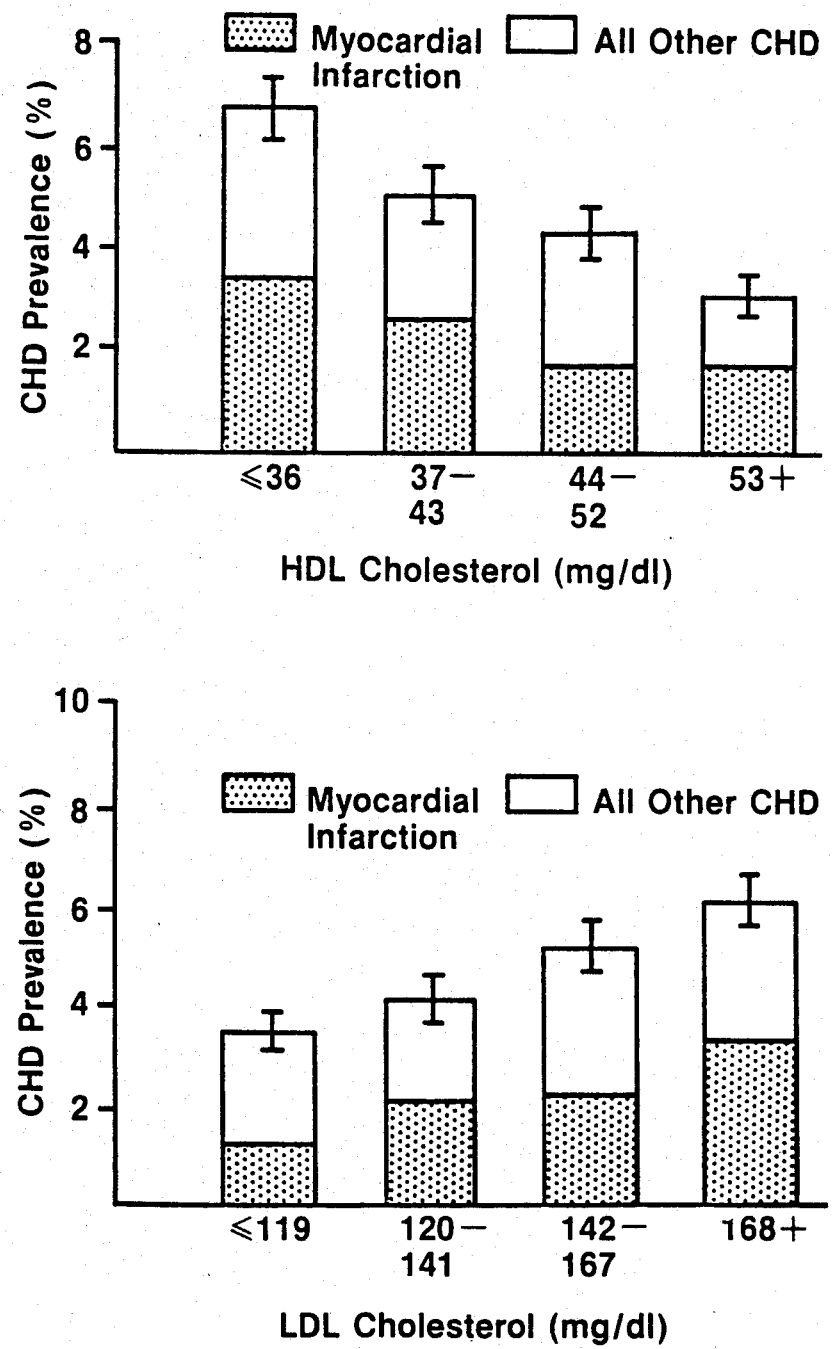
FIG. 1 graphically depicts the correlation between the occurrence of coronary heart disease and the amounts of either HDL or LDL cholesterol

The peptides of the present invention exhibit a specific arrangement of amino acid residues which results in an idealized amphipathic helix. As noted above, the specific positioning of negatively-charged, positively-charged, and hydrophobic residues is critical to the formation of the amphipathic helix, and thus to the intended functioning of the peptide. Analogues having the positive and negative residues reversed from the placement of charged residues occurring in native apoproteins show little or no lipid association. In the 18-residue sequence of the subject peptides, positively-charged residues (the "C" group of formula I) are required in positions 4, 9, 13 and 15; negatively-charged residues (the "A" group of formula I) are necessary at positions 1, 8, 12 and 16. Hydrophobic residues (the "B" group of formula I) should be placed at positions 2, 3, 6, 7, 10, 11, 14, 17 and 18. The residues serine, threonine, alanine, glycine or histidine are preferred at position 5 ("D"). The specific residues chosen to occupy particular functional positions, e.g., positively-charged positions, may be varied without undue adverse effect on the activity of the peptide. For example, the negatively-charged residues aspartic acid and glutamic acid may be interchanged at any position in the sequence in which a negatively-charged residue is called for. Similarly, lysine or arginine may be placed at any of the positively-charged positions. The preferred hydrophobic residues are tryptophan, phenylalanine, alanine, leucine, isoleucine, valine and $\alpha$-naphthylalanine.

In one embodiment of the present invention, many of the hydrophobic residue positions are occupied by $\alpha$-naphthylalanine. A preferred embodiment of the present invention is one in which the sequence is Asp-Trp-$\alpha$Nal-Lys-Ala-Phe-$\alpha$Nal-Asp-Lys-$\alpha$Nal-Ala-Glu-Lys-$\alpha$Nal-Lys-Glu-Ala-Phe (18naA).

The amino acids used may be naturally occurring forms, or synthetic amino acids which exhibit exceptional desirable qualities may be employed. For example, the synthetic amino acid $\alpha$-naphthylalanine shows a greater degree of hydrophobicity than any of the naturally occurring amino acids, and is particularly useful in the peptides of the present invention. Similarly, the substituted amino acid dimethyl lysine is more highly positively-charged than unsubstituted lysine, and may be preferred in certain embodiments. Thus, the substitution of useful analogues or homologues of the naturally occurring amino acids required in the subject peptides is also contemplated. Either D- or L-forms of amino acids are suitable for use in the present invention.

Although the essential functional amphipathic helix of the present invention consists of a sequence of eighteen amino acids, additions to either end of the eighteen residue peptides may be accomplished without substantially affecting the capacity for helix formation. For example, an extending tripeptide may be added at each end of the basic amphipathic peptide chain to minimize helical end effects. Multiple amphipathic helical domains may also prove useful. Thirty-seven residue peptides which consist of two eighteen residue peptides connected by, for example, proline, also show the ability to form discoidal complexes with phospholipid and to displace native apoproteins from HDL. However, for the present scheme, the eighteen residue unit appears to be critical to the formation of a proper helix. Deletion of an amino acid at, for example, the 10th position in the sequence will cause rotation of the polar-nonpolar interface by 100°, and results in a peptide which essentially lacks the capacity to displace native apoproteins from HDL.

The products of the invention may be synthesized by any number of techniques now available for synthesis of simple and complex low molecular weight proteins. Generally speaking, these techniques involve stepwise synthesis by successive additions of amino acids to produce progressively larger molecules. The amino acids are linked together by condensation between the carboxyl group of one amino acid and the amino group of another amino acid to form a peptide bond. To control these reactions, it is necessary to block the amino group of one acid and the carboxyl group of the other. The blocking groups should be selected for easy removal without adversely affecting the polypeptides, either by racemization or by hydrolysis of formed peptide bonds. Certain amino acids have additional functional groups, such as the hydroxyl group of tyrosine. It is usually necessary to block these additional groups with an easily removed blocking agent, so that it does not interfere with the desired condensation for the formation of peptide bonds.

A wide variety of procedures exist for the synthesis of polypeptides, and a wide variety of blocking agents have also been devised. Most of these procedures are applicable to the peptides of the present invention. The presently preferred method for synthesis of the subject peptides is the Merrifield technique. In this procedure, an amino acid is bound to a resin particle as an ester bond, and the peptide is generated in a stepwise manner by successive additions of protected amino acids to the growing chain. The general procedure is well known, and has been described in many articles, for example: Merrifield, R. B., Jour. Amer. Chem. Soc. 96, 2986-2993, 1964.

However, a modification of the known procedure avoids the usual HF-step for the release of the peptide from the solid support by a transfer hydrogenation procedure with formic acid used as the acid donor instead. This procedure, which is outlined more fully in Example 1, results in the release of a nearly pure peptide, as well as the removal of protecting groups from the $\epsilon$—$NH_2$ groups of lysine, benzyl esters from aspartic acid and glutamic acid, and the benzyl ether from tyrosine.

The peptides of the present invention are intended for use in the formation of synthetic high density lipoprotein. Peptides of formula (I) herein have been shown to spontaneously interact at room temperature with phospholipid to form small, soluble, discoidal HDL-like complexes. These synthetic complexes may then be used as substitute high-density lipoprotein in the plasma, providing the same protective effect against atherosclerosis in the bloodstream as native HDL would. The phospholipid used for formation of the complex may vary, but among the most preferred are egg phosphatidylcholine (PC), dimyristoyl phosphatidylcholine (DMPC), and dipalmitoyl phosphatidylcholine (DPPC).

The mode of administration of the peptide-phospholipid complex is preferably parenteral, i.e., intravenous, intraperitoneal, intramuscular, or subcutaneous, with intravenous administration being most preferred. The synthetic complexes may be administered alone, without a carrier vehicle; however they may also be administered with pharmaceutically acceptable non-toxic carriers, the proportions of which are determined by the suitability and chemical nature of the particular carrier. For intravenous or intramuscular administration, they may be used in the form of a sterile solution containing other solutes, for example, sufficient saline or glucose to make the solution isotonic. Like insulin, the peptides of the subject invention may also prove to be administrable by use of a continuous perfusion device, which should simplify the method of administration.

The physician will determine the dosage which will be most suitable for a particular situation. Dosage will generally depend upon the size of the patient, and to some extent, the seriousness of the condition to be treated. A normal dosage will generally be in the range of 200-600 mg peptide per day.

The following examples, which are for illustrative purposes only, more clearly demonstrate the principles and practice of the subject invention.

EXAMPLE 1

The peptides of the present invention may be synthesized using the following general procedure:

A solid-phase peptide synthesis technique is employed, using a benzhydrylamine polystyrene cross-linked with 1% divinyl benzene as the solid support. The C-terminal tert-butyloxycarbonyl Boc-Phe is attached to the solid support through a phenylacetamidomethyl (PAM) group. Deprotection of $\alpha$-Boc at each stage is carried out with 40% trifluoroacetic acid in $CH_2Cl_2$ (10% anisole and 1% mercaptoethanol are added as scavengers). The following side chain protections may be used for bi-functional amino acids: benzyloxycarbonyl for lysine, benzyl esters for the carboxyls of aspartic and glutamic acids, benzyl ether for the OH of tyrosine, and formyl for indole of tryptophan.

Stepwise coupling of each amino acid is carried out using three equivalents of each Boc-amino acid, dicyclohexylcarbodiimide, and 1-hydroxybenzotriazole. The couplings are monitored by the Kaiser test. Release of peptides from the solid support is achieved by using transfer hydrogenation using dimethyl formamide (DMF; 20 ml/g of the peptide resin). Palladium acetate (in an amount equal to the weight of the peptide resin) is used as a catalyst with formic acid (5% total concentration with respect to DMF) serving as the hydrogen donor. Reactions are carried out at room temperature for 15 to 24 hours. The catalyst and polymer are filtered off, and washed with 50% acetic acid. The filtrate and washing are diluted with water and lyophilized to obtain the crude peptides. The indole protection on tryptophan is removed using hydroxylamine hydrochloride at pH 9.5.

The peptides may then be purified by HPLC on a C-18 silica column and characterized by HPLC amino acid analysis, sequencing and TLC.

EXAMPLE 2

The following example illustrates the preparation of 18naA:

Boc-Phe was converted to Boc-Phe-Oxymethyl-phenylacetic acid (Boc-Phe-PAM) following the procedure of Mitchell, et al. (Mitchell, A. R., Kent, S. B. H., Englehard, M., and Merrifield, R. B., J. Org. Chem. 43, 2845-2852, 1978). This was then coupled to benzhydrylamine resin (1.1 g, 0.45 mM of $NH_2$/g of resin) by treatment with three equivalents each of Boc-Phe-PAM, 1-hydroxybenzotriazole and dicyclohexylcarbodiimide, for 3 h. The coupling reaction was monitored by the Kaiser's test. The following schedule was used for the solid phase peptide synthesis:

| STEP | REAGENTS | NO. OF CYCLES | VOLUME | TIME (MIN) |
|---|---|---|---|---|
| 1 | $CH_2Cl_2$ | 2 | 30 ml | 2 |
| 2 | 40% TFA in $CH_2Cl_2$ (10% anisole: 1% mercaptoethanol) | 1 | 30 ml | 5 |
| 3 | 40% TFA in $CH_2Cl_2$ (10% anisole: 1% | 1 | 30 ml | 25 |

| STEP | REAGENTS | NO. OF CYCLES | VOL-UME | TIME (MIN) |
|------|----------|---------------|---------|------------|
| | mercaptoethanol) | | | |
| 4 | $CH_2Cl_2$ | 2 | 30 ml | 2 |
| 5 | 10% DIEA in $CH_2Cl_2$ | 2 | 40 ml | 5 |
| 6 | $CH_2Cl_2$ | 2 | 30 ml | 2 |
| 7 | Boc Amino acid + HOBt (3 equts each in 1:1 $CH_2Cl_2$:DMF) + DCC (3 equts in 1:1 $CH_2Cl_2$:DMF) | | 20 ml 10 ml | 2 120–360 |
| 8 | $CH_2Cl_2$ | 2 | 30 ml | 2 |
| 9 | t-Butanol (10% isoamyl alcohol) | 3 | 30 ml | 2 |
| 10 | $CH_2Cl_2$ | 2 | 30 ml | 2 |
| 11 | Kaiser's Test-- if positive, repeat steps 4 to 10; if negative, proceed to next amino acid. | | | |

Following the completion of the sequence, steps 1 to 6 were repeated, the peptide resin was dried and weighed (1.7 g).

Release of the peptide from the resin was accomplished by stirring the peptide resin (800 mg) in 30 ml of DMF in presence of palladium acetate (800 mg) (equilibration time 2 h) and 85% formic acid (1.5 ml) for 15 h. The reaction mixture was diluted with ether (500 ml) and filtered. The residue was washed with 50% acetic acid, diluted with water and lyophilized to obtain 230 mg of the peptide. This was then treated with 0.1M hydroxylamine hydrochloride solution (pH 9.5 100 ml) for 15 h. The pH was adjusted to 6.0 when a precipitate appeared which was isolated by centrifugation and washed with 20 ml of water. The residue was then dissolved in 50 ml of 50% acetonitrile (0.1% TFA), diluted and lyophilized to yield 140 mg.

This was further purified by injecting a solution of the compound (40 mg in 0.5 ml of 52.5% acetonitrile (0.1% TFA)) on a previously equilibrated (with 52.5% acetonitrile 0.1% TFA) C-18 Silica column (particle size 13–24, Michel Miller glass column, 22 mM ID×300 mM, pressure 40 psi, flow rate 2 ml/min. monitored at 220 nM). 2 min. fractions were collected and each fraction was subjected to TLC analysis (n-butanol:acetic acid:water:ethyl acetate 1:1:1:1). TLC indicated the presence of pure material in fractions 20–36 which were pooled and lyophilized to obtain 22 mg of the pure peptide.

EXAMPLE 3

The phospholipid associating properties of synthetic amphipathic peptides can be demonstrated by using small, unilamellar vesicles of egg phosphatidylcholine (PC) or dimyristoyl phosphatidylcholine (DMPC). A solution of PC or DMPC in ethanol is taken to dryness under reduced pressure, lyophilized overnight, and allowed to swell in 2 mM N-[tris(hydroxymethyl)methyl-2-amino]ethanesulfonic acid (Tes), 2 mM histidine, 0.15M NaCl, pH 7.4 with mixing for 2 hours until completely hydrated. The liposomes are then sonicated under argon either in a bath sonicator (Laboratory Supplies Co.; Hicksville N.Y.) at temperatures from 15°–30° C. for 15 minutes, or until the solution is clear; or, a Branson W200P probe sonicator at 0° C. for 1 hour at 50% output. When radiolabeled lipid is used, 0.01 µCi of uniformly labeled [$^{14}$C] PC (Applied Science; State College Pa.) is added to the PC before rotary evaporation. Radiolabeled $^{125}$I-peptide is prepared using the iodine-125-monochloride method (A. S. McFarane, Nature 182:53, 1958). For purposes of comparison, apolipoproteins A-I and C-III are isolated from human serum using standard chromatographic procedures.

The peptides or apolipoproteins are dissolved in a small volume of Tes-histidine-buffer (2 mM Tes, 2 mM histidine, 0.15M NaCl, pH 7.4) to give concentrations ranging from 0.01 to 3 mM. Peptide lipid asociation is examined by incubating the peptide and lipid together at 23° C. for a period of 24 hours prior to equilibrium density gradient centrifugation. Cholate dialysis is required to produce discoidal structures for peptide complexes with egg PC; Peptide-DMPC discoidal complexes form spontaneously.

Figure 8B:
FIG. 8 shows a comparison of the configuration of Apo A-1/DMPC complexes and peptide/DMPC complexes (from an electron micrograph).
Figure 8A:
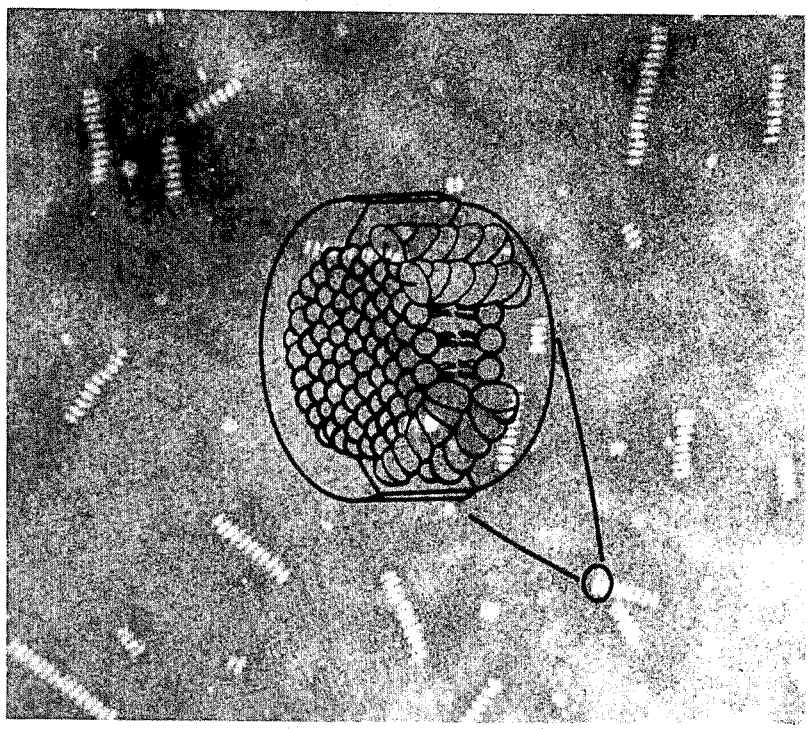

Lipid association studies have been performed with the synthetic amphipathic peptides 18naA, 18A (Asp-Trp-Leu-Lys-Ala-Phe-Tyr-Asp-Lys-Val-Ala-Glu-Lys-Leu-Lys-Glu-Ala-Phe; P. Kanellis et al., J. Biol. Chem. 255, 11464–11472, 1980), 18rA (a variation of 18A in which all the charges are reversed), 17 desA, a variation of 18A in which the valine residue has been removed, and 37pA (a 37-peptide in which two 18A sequences are joined together by a proline residue); Each has been tested to demonstrate the ability to form complexes with phospholipid. At room temperature, 18A, 18naA and 37pA spontaneously interact with multilamellar dimyristoylphosphatidylcholine vesicles to form small soluble complexes that, on the basis of negative stain electron microscopy, are discoidal in shape (see FIG. 8).

Figure 7:
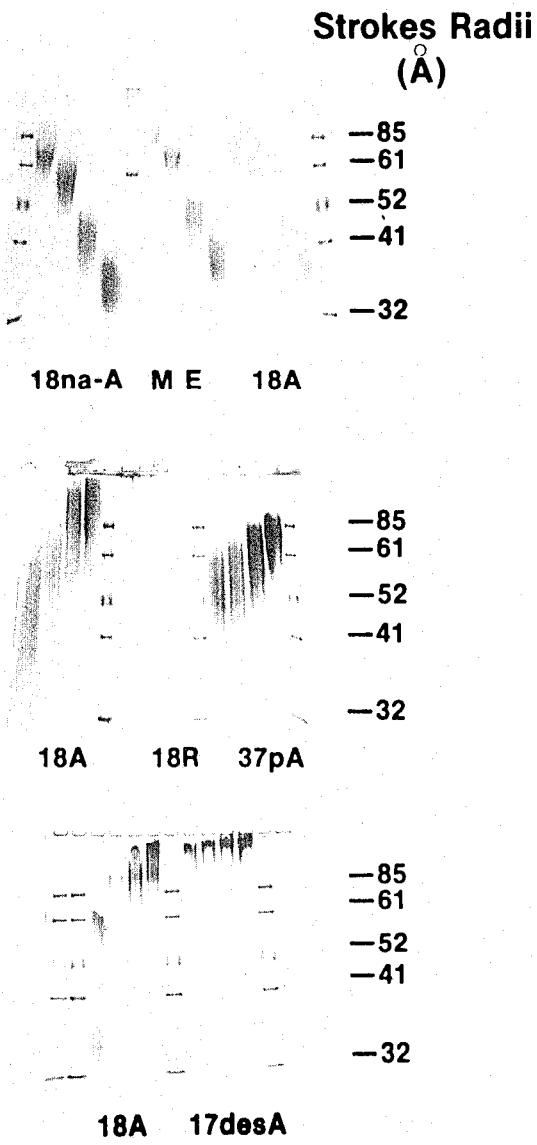
FIG. 7 shows pore exclusion gradient electrophoresis of various amphipathic peptide/lipid complexes.

Pore exclusion electrophoresis was performed on the resulting peptide/lipid complexes (FIG. 7), on 4–25% olyacrylamide gels using non-denaturing conditions for 24 to 36 hours. Gels were fixed and stained in the presence of 4% formaldehyde. DMPC is mixed with a trace of fluorescent marker (NBD). Different ratios of protein:lipid (1:1, 1:2.5, 1:5, 1:7.5) were incubated for 24–36 hours.

The following table compares the size of these HDL-like complexes formed by various synthetic peptides. Note that for Apo A-1, stokes diameter varies from 80–200Å.

| SIZE OF PARTICLES AT DIFFERING RATIO OF PEPTIDE TO LIPID BY GRADIENT GEL: STOKES DIAMETER, A | | | | |
|---|---|---|---|---|
| Protein: Lipid | 18A | 37pA | 18naA | 18rA* |
| 1:1 | 90 | 110 | 75 | 200 |
| 1:2.5 | 120 | 115 | 90 | 200 |
| 1.5 | 170 | 130 | 115 | 200 |
| 1.75 | 200 | 160 | 140 | 200 |

*18rA does not enter the gel at all, indicating that it does not form a stable complex. For Apo A-I, Stokes diameter varies from 80–200Å.

EXAMPLE 4

Figure 2:
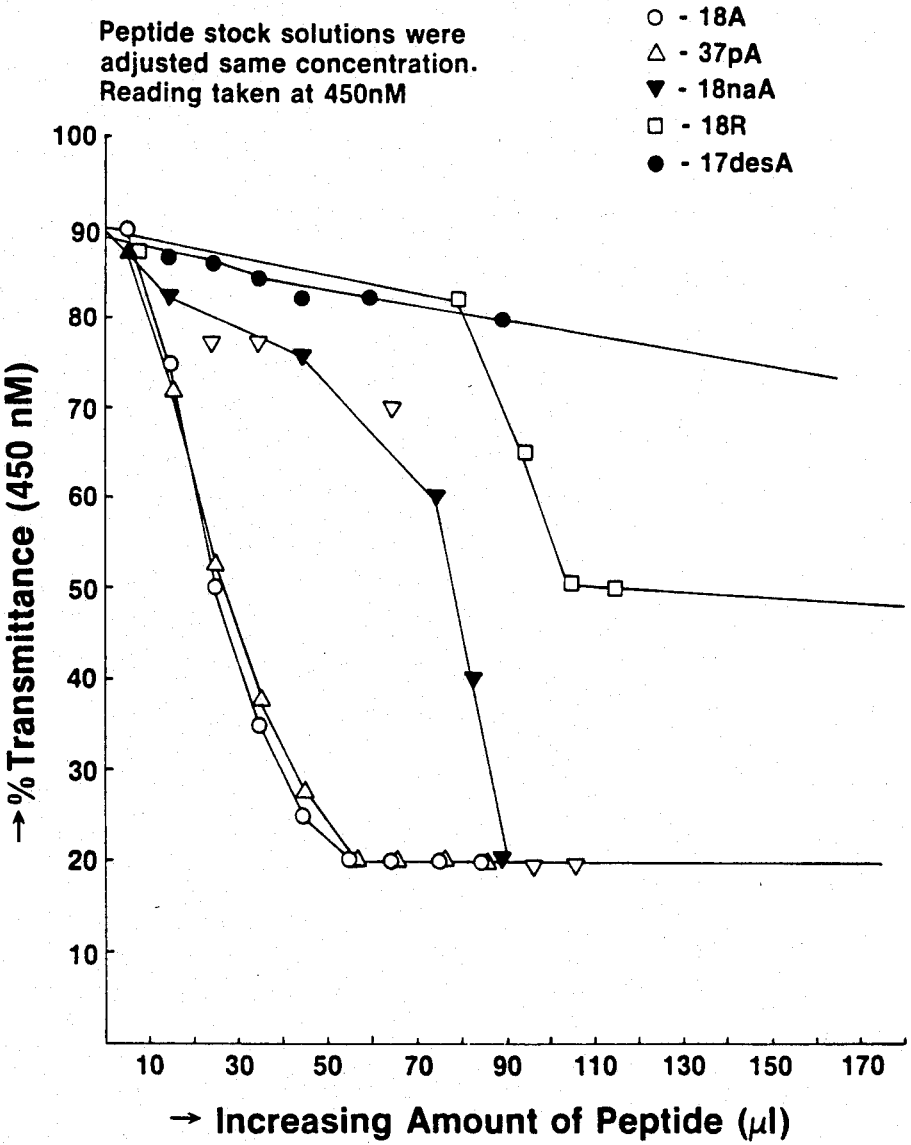
FIG. 2 shows the results of a turbidity clearance study utilizing several different amphipathic peptides.
Figure 3:
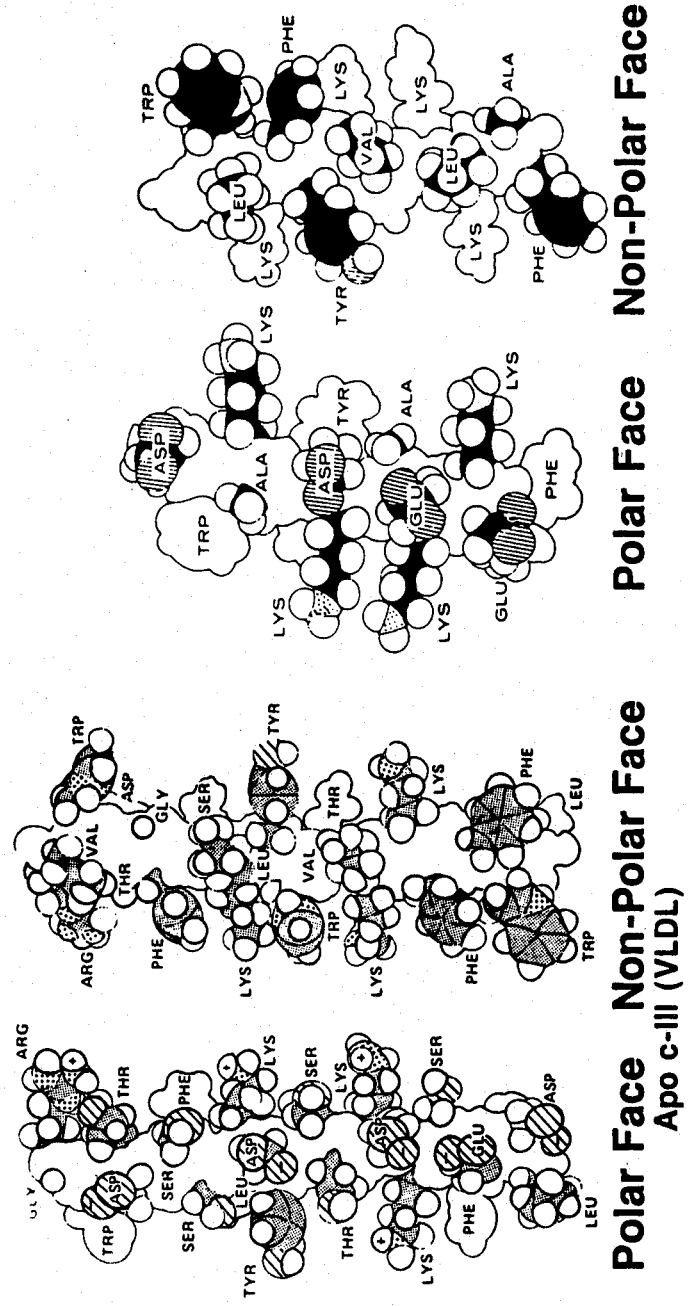
FIG. 3 shows the diagrammatic representations of naturally occurring and synthetic amphipathic helices.
Figure 4:
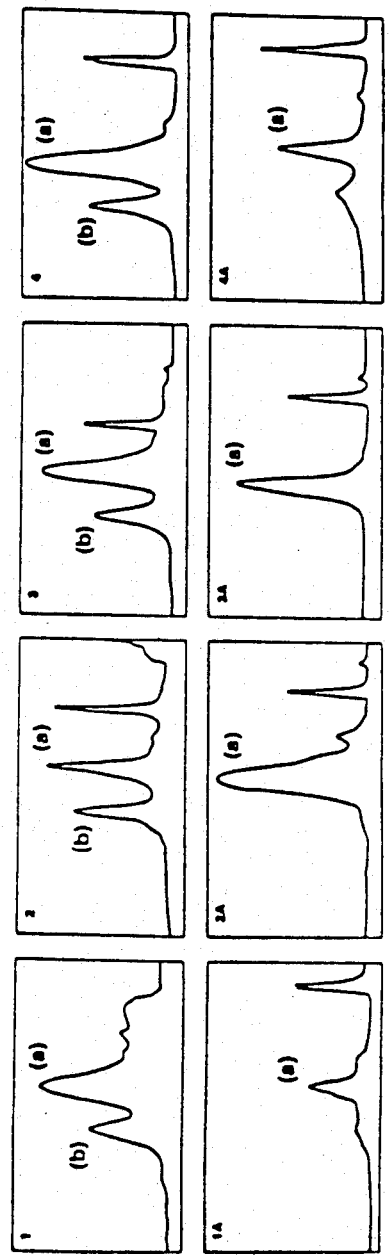
FIG. 4 demonstrates the results of apolipoprotein-displacement studies utilizing various amphipathic peptides.
Figure 5:
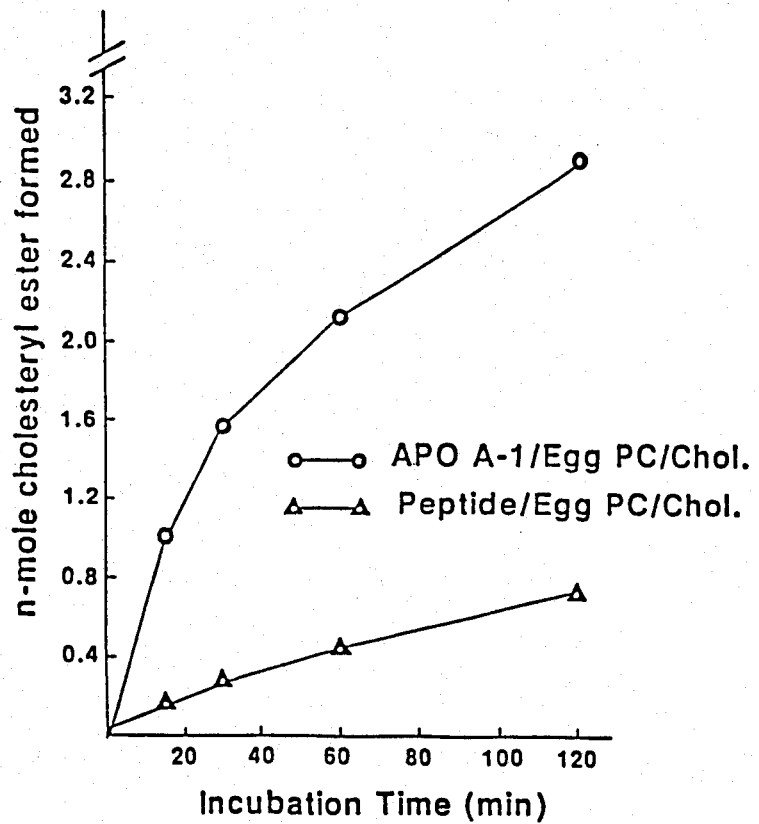
FIG. 5 shows a comparison of the capacity of discoidal complexes of Apo A-1/Egg PC/cholesterol and a synthetic amphipathic peptide/Egg PC/cholesterol to stimulate LCAT activity.
Figure 6:
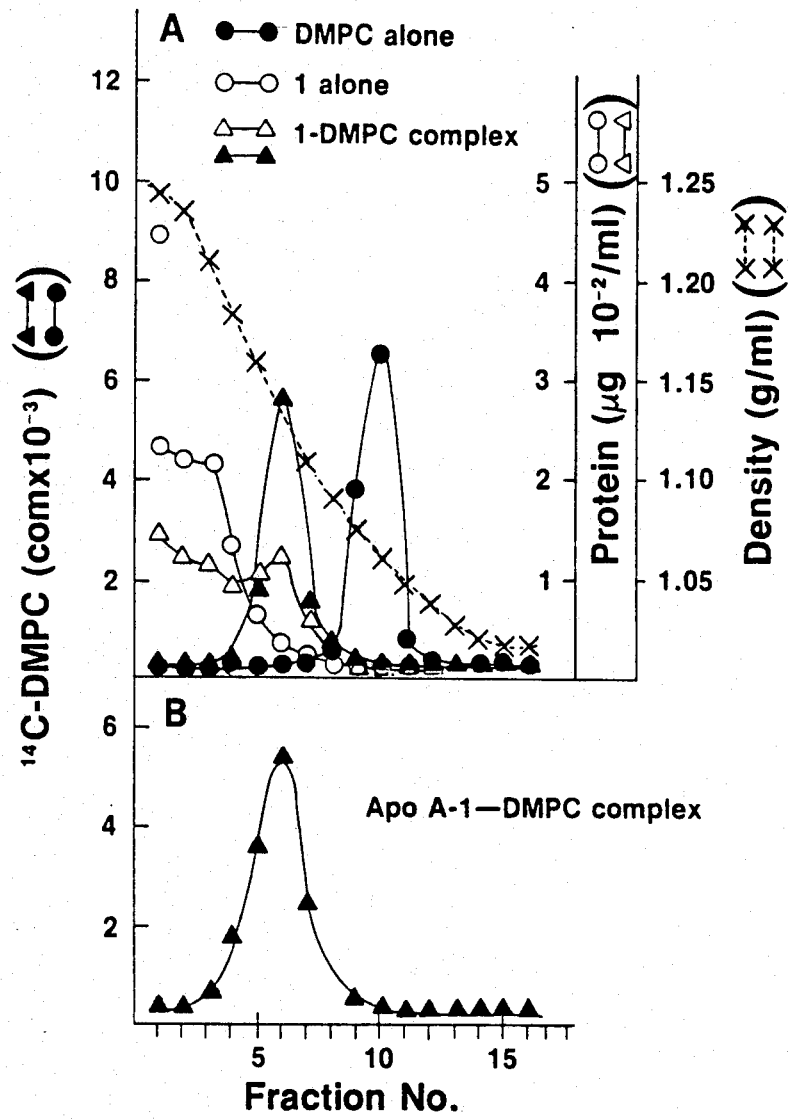
FIG. 6 shows the distribution of protein and phospholipid in density gradient fractions of synthetic peptide/DMPC complexes, DMPC, synthetic peptide alone, and Apo A-1/DMPC complexes.

The following procedure was followed for the turbidity clearance studies shown in FIG. 2:

1 mg of DMPC is vortexed in 1 ml of phosphate buffer, and then diluted with 10 ml with the same buffer. A 5 ml aliquot of this turbid solution is then placed in a cuvette and increasing amounts of a synthetic peptide containing solution is added. As more peptide is added, and if the peptide does form complexes with the lipid, the turbidity eventually decreases.

The above procedure was conducted using the peptides 18A, 18naA, 37pA, 18rA, and 17desA, a variation of 18A from which the valine residue is removed. Increasing transmittance was recorded in an AMENCO SPF-500.

Further comparisons of this series of peptides with native apolipoproteins is found in Table 2.

TABLE 2

PROPERTIES OF SYNTHETIC AMPHIPATHIC PEPTIDES VERSUS AMPHIPATHIC HELICAL DOMAINS OF APOLIPOPROTEINS

| | Mean hydrophobicity index of nonpolar face | | | | |
|---|---|---|---|---|---|
| | Considering positively charged residues[a] | Not considering positively charged residues | Residue length | Residue position in polypeptide chain | Number of ion pairs |
| 18A series peptides | 6.0 | 3.8 | 18 | 4–21 | 4 |
| Apo A-I | 4.7 | 3.5 | 26 | 8–33 | 3 |
| APO A-I | 3.6 | 1.7 | 14 | 131–144 | 3 |
| Apo A-II | 4.7 | 3.3 | 21 | 10–30 | 3 |
| Apo A-II | 5.0 | 2.3 | 11 | 39–49 | 2 |
| Apo C-I | 4.5 | 2.8 | 21 | 33–531 | 4 |
| Apo C-I | 4.8 | 3.0 | 12 | 12–29 | 3 |
| Apo C-III | 4.8 | 3.5 | 28 | 40–67 | 4 |
| Amyloid A | 4.5 | 3.5 | 24 | 2–25 | 4 |

[a]Calculated as described previously in SEgrest and Feldmann, Biopolymers 16, 2053–2065, 1977 with the additional modification that arginyl residues at the polar-nonpolar interface are assigned a hydrophobicity index of 3.0 (on this scale, alanyl = 1.0 and tryptophanyl = 6.5) and entered into the calculation in the same manner as lysyl residues. The abbreviation Apo is used for apolipoprotein.

What we claim is:

1. A peptide capable of forming an amphipathic helix, said peptide having the sequence Asp-Trp-αNal-Lys-Ala-Phe-αNal-Asp-Lys-αNal-Ala-Glu-Lys-αNal-Lys-Glu-Ala-Phe.

2. A synthetic high density lipoprotein which comprises a peptide capable of forming an amphipathic helix, said peptide having the sequence: Asp-Trp-αNal-Lys-Ala-Phe-αNal-Asp-Lys-αNal-Ala-Glu-Lys-αNal-Lys-Glu-Ala-Phe.

3. The lipoprotein of claim 2 wherein the phospholipid is phosphatidylcholine, dimyristyl phosphatidyl chlorine or dipalmitoyl phosphatidylcholine.

4. A therapeutic composition useful in the treatment and prevention of atherosclerosis which comprises the synthetic lipoprotein of claim 2, in combination with a pharmaceutically acceptable carrier.

5. A method of treatment or prevention of atherosclerosis which comprises administering to a host in need of such treatment an effective amount of a syntheic lipoprotein comprising a peptide having the sequence: Asp-Trp-Leu-Lys-Ala-Phe-Tyr-Asp-Lys-Val-Ala-Glu-Lys-Leu-Lys-Gly-Ala-Phe; bound to a phospholipid.

6. A method of treatment or prevention of atherosclerosis which comprises administering to a host in need of such treatment an effective amount of a synthetic lipoprotein comprising a peptide having the sequence: Asp-Trp-αNal-Lys-Ala-Phe-αNal-Asp-Lys-αNal-Ala-Glu-Lys-αNal-Lys-Glu-Ala-Phe; bound to a phospholipid.

7. A method of treatment or prevention of atherosclerosis which comprises administering to a host in need of such treatment an effect amount of a synthetic lipoprotein comprising a peptide having the sequence: Asp-Trp-Leu-Lys-Ala-Phe-Tyr-Asp-Lys-Val-Ala-Glu-Lys-Leu-Lys-Gly-Ala-Phe-Pro-Asp-Trp-Leu-Lys-Ala-Phe-Tyr-Asp-Lys-Val-Ala-Glu-Lys-Leu-Lys-Gly-Ala-Phe; bound to a phospholipid.

* * * * *